United States Patent
Komuro et al.

(10) Patent No.: US 11,337,587 B2
(45) Date of Patent: May 24, 2022

(54) MEDICAL OVER-TUBE, AND MEDICAL DEVICE ADAPTER HAVING MOVING MEMBER AND MEDICAL SYSTEM HAVING SUCH MEDICAL OVER-TUBE

(71) Applicant: Olympus Corporation, Hachioji (JP)

(72) Inventors: Ryohei Komuro, Hirosaki (JP); Hiroshi Hashi, Tokyo (JP); Takumi Isoda, Hachioji (JP); Shotaro Takemoto, Tokyo (JP); Tatsutoshi Hashimoto, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 863 days.

(21) Appl. No.: 16/189,872

(22) Filed: Nov. 13, 2018

(65) Prior Publication Data

US 2019/0076003 A1    Mar. 14, 2019

Related U.S. Application Data

(63) Continuation of application No. PCT/JP2016/089018, filed on Dec. 28, 2016.

(51) Int. Cl.
*A61B 1/012* (2006.01)
*A61B 34/30* (2016.01)
(Continued)

(52) U.S. Cl.
CPC ........ *A61B 1/00135* (2013.01); *A61B 1/0016* (2013.01); *A61B 1/00064* (2013.01);
(Continued)

(58) Field of Classification Search
CPC ............ A61B 1/00098; A61B 1/00133; A61B 1/00149; A61B 1/00154
See application file for complete search history.

(56) References Cited

U.S. PATENT DOCUMENTS 4,854,301 A * 8/1989 Nakajima .......... A61B 1/00147
600/102
6,451,027 B1 * 9/2002 Cooper .............. A61B 1/00149
606/130
(Continued)

FOREIGN PATENT DOCUMENTS

JP   2009268889   11/2009
JP   2009544430   12/2009
(Continued)

OTHER PUBLICATIONS

International Search Report and Written Opinion from corresponding International Application No. PCT/JP2016/089018 dated Mar. 21, 2017.
(Continued)

*Primary Examiner* — John P Leubecker
(74) *Attorney, Agent, or Firm* — Scully, Scott, Murphy & Presser, P.C.

(57) ABSTRACT

A medical system includes a medical device, an over-tube, and a console. The medical device includes an insertion portion. The over-tube is configured to receive the insertion portion. A console having a first connector is attached to the medical device and a second connector is attached to the over-tube. The over-tube has a tubular main body and a proximal-end portion. The proximal-end portion comprises a tubular member having an insertion port for receiving the insertion portion of the medical device therethrough. A base portion is coupled to the second connector and a moving mechanism is coupled to both the tubular member and the base portion. The moving mechanism is configured to cause the tubular member to move with respect to the second connector such that the tubular member has two or more degrees of freedom with respect to the second connector.

10 Claims, 11 Drawing Sheets

(51) Int. Cl.
*A61B 17/00* (2006.01)
*A61B 1/00* (2006.01)
*A61B 34/37* (2016.01)
*A61B 34/00* (2016.01)
*A61B 1/31* (2006.01)

(52) U.S. Cl.
CPC .......... *A61B 1/00121* (2013.01); *A61B 1/012* (2013.01); *A61B 1/31* (2013.01); *A61B 34/30* (2016.02); *A61B 34/37* (2016.02); *A61B 34/74* (2016.02); *A61B 2017/00477* (2013.01); *A61B 2034/301* (2016.02); *A61B 2034/305* (2016.02); *A61B 2034/742* (2016.02)

(56) References Cited

U.S. PATENT DOCUMENTS

| | | | |
|---|---|---|---|
| 6,554,793 B1* | 4/2003 | Pauker | A61B 1/00151 604/158 |
| 2005/0234294 A1* | 10/2005 | Saadat | A61B 1/00098 600/104 |
| 2005/0234297 A1* | 10/2005 | Devierre | A61B 1/00098 600/153 |
| 2007/0156123 A1 | 7/2007 | Moll et al. | |
| 2007/0167682 A1* | 7/2007 | Goldfarb | A61B 1/00154 600/114 |
| 2007/0197896 A1 | 8/2007 | Moll et al. | |
| 2008/0027464 A1 | 1/2008 | Moll et al. | |
| 2009/0281378 A1 | 11/2009 | Banju et al. | |
| 2010/0082041 A1 | 4/2010 | Prisco | |
| 2011/0152609 A1* | 6/2011 | Trusty | A61B 90/50 600/102 |
| 2011/0270273 A1 | 11/2011 | Moll et al. | |
| 2012/0118088 A1* | 5/2012 | Smith | A61B 90/57 74/89.2 |
| 2012/0289973 A1 | 11/2012 | Prisco et al. | |
| 2013/0165908 A1* | 6/2013 | Purdy | A61B 1/00149 606/1 |
| 2013/0331857 A9 | 12/2013 | Prisco et al. | |
| 2014/0236175 A1 | 8/2014 | Cooper et al. | |
| 2014/0378761 A1* | 12/2014 | Zorn | A61B 1/0016 600/104 |
| 2016/0030124 A1 | 2/2016 | Kishi et al. | |
| 2016/0135662 A1 | 5/2016 | Hatakeyama et al. | |
| 2016/0310115 A1 | 10/2016 | Prisco, Sr. et al. | |
| 2017/0007346 A1 | 1/2017 | Kikuchi | |
| 2017/0119412 A1* | 5/2017 | Noonan | A61B 1/00149 |
| 2017/0151028 A1 | 6/2017 | Ogawa et al. | |
| 2017/0239009 A1 | 8/2017 | Cooper et al. | |
| 2018/0055588 A1 | 3/2018 | Yanagihara et al. | |

FOREIGN PATENT DOCUMENTS

| | | |
|---|---|---|
| JP | 2014521375 | 8/2014 |
| JP | 2015024033 | 2/2015 |
| JP | 2015-533525 A | 11/2015 |
| JP | 2015198819 | 11/2015 |
| JP | 2016506859 | 3/2016 |
| JP | 2016511013 | 4/2016 |
| WO | 2007070693 | 6/2007 |
| WO | 2008014425 | 1/2008 |
| WO | 2012158449 | 11/2012 |
| WO | 2014127271 | 8/2014 |
| WO | 2016194262 | 12/2016 |

OTHER PUBLICATIONS

Japanese Office Action dated Apr. 28, 2020 in Japanese Patent Application No. 2018-558590.

* cited by examiner

FIG.16
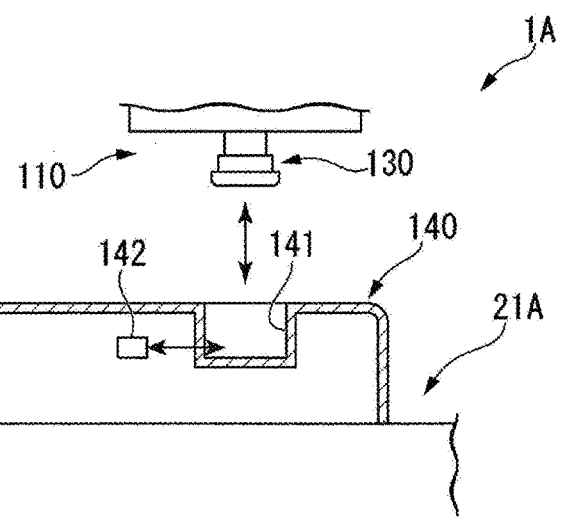
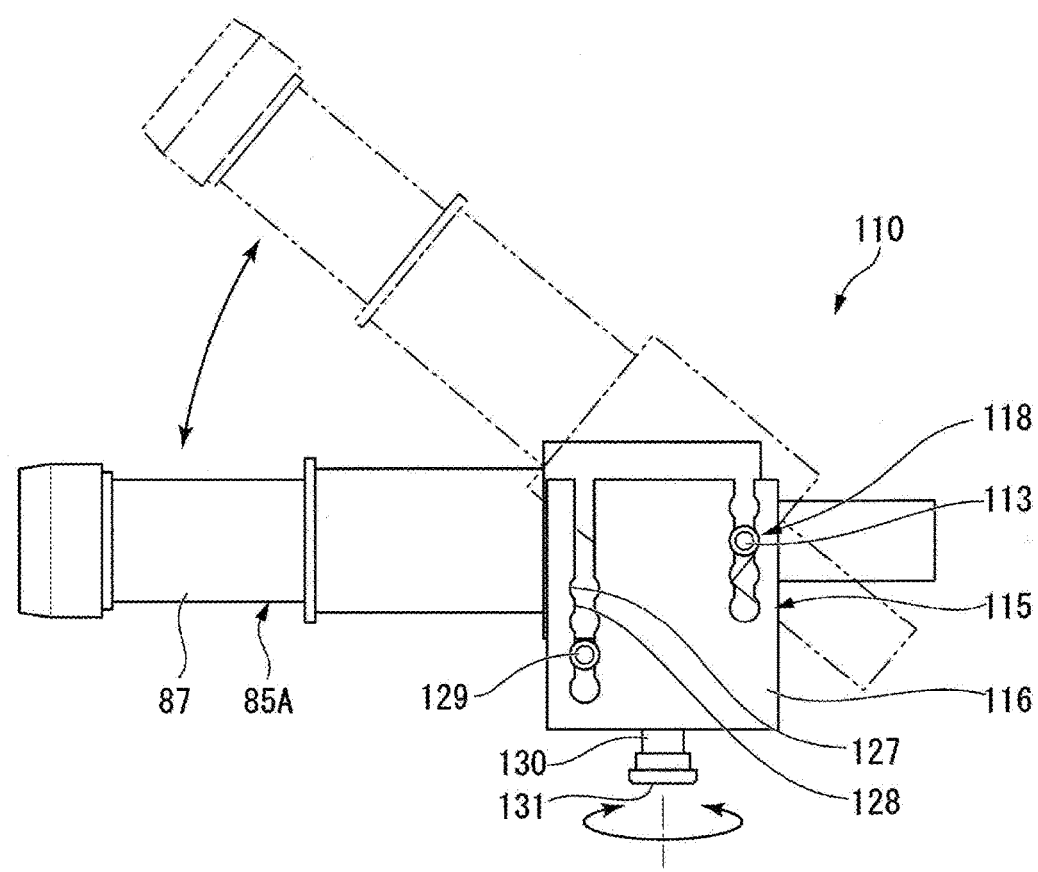
FIG.17

MEDICAL OVER-TUBE, AND MEDICAL DEVICE ADAPTER HAVING MOVING MEMBER AND MEDICAL SYSTEM HAVING SUCH MEDICAL OVER-TUBE

CROSS-REFERENCE TO RELATED APPLICATION

This application is a continuation application of PCT Application No. PCT/JP2016/089018 filed on Dec. 28, 2016, which is hereby incorporated by reference in its entirety.

TECHNICAL FIELD

The technology disclosed herein relates generally to a medical system, and more specifically, a medical system having a medical over-tube, and a medical device adapter.

DESCRIPTION OF THE RELATED ART

There have been known medical systems in which a medical device is inserted into the body of a patient to perform a treatment therein. For example, Japanese Patent Application JP-T-2009-544430 discloses a system having a device driver and a control station. A device assembly is attached to the device driver and is inserted into the body of a patient as a medical device. The control station is connected to the device driver for remotely controlling the device assembly and the device driver.

The medical device is detachably attached to a medical system, can be connected and disconnected to the medical system when necessary, and is operated in response to motive power transmitted under remote control. For example, Japanese Patent Application JP-T-2014-521375 discloses an interface for connecting and disconnecting a medical device without causing the medical device to operate unintentionally at the time when is not in operation. In addition, Japanese Patent Applications JP-A-2015-024033 and JP-T-2015-198819 disclose medical devices that are remotely controlled from outside the body of a patient and operate, for example, by moving forward or backward and/or rotating in the body of the patient.

BRIEF SUMMARY OF EMBODIMENTS

One aspect of the technology disclosed herein is directed to a medical system comprising a medical device having an insertion portion. An over-tube is configured to receive the insertion portion of the medical device so as to be inserted into a body of a patient. A console having a first connector is attached to the medical device and a second connector is attached to the over-tube. The over-tube has a tubular main body, and a proximal-end portion coupled to the tubular main body. The proximal-end portion comprises a tubular member having an insertion port for receiving the insertion portion of the medical device therethrough. A base portion is coupled to the second connector and a moving mechanism is coupled to both the tubular member and the base portion. The moving mechanism is configured to cause the tubular member to move with respect to the second connector such that the tubular member has two or more degrees of freedom with respect to the second connector.

Another aspect of the technology disclosed herein is directed to a medical over-tube used within an elongated medical device comprises a tubular main body configured to receive an insertion portion of the elongated medical device. A proximal-end portion is coupled to the tubular main body. The proximal-end portion comprises a tubular member having an insertion port configured to receive the insertion portion of the elongated medical device therethrough. A base portion is coupled to an instrument different from the elongated medical device. A moving mechanism is coupled to the tubular member and the base portion. The moving mechanism is configured so as to cause the tubular member to move with respect to the base portion such that the tubular member has two or more degrees of freedom with respect to the base portion.

A further aspect of the technology disclosed herein is directed to a medical device adapter for connecting a medical device to a chassis. The medical device adapter comprises a tubular member configured to receive an insertion portion of the medical device therethrough. A base portion is detachably coupled to the chassis with one or more degrees of freedom. A moving mechanism is coupled to the tubular member and the base portion. The moving mechanism is configured to cause the tubular member to move with respect to the base portion such that the tubular member has one or more degrees of freedom with respect to the base portion.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 16 is a schematic partly cross-sectional view depicting a configurational example of a console on which the medical device adapter is to be attached.

FIG. 17 is a side elevational view depicting the manner in which the medical device adapter operates with respect to the treatment tool unit.

DETAILED DESCRIPTION OF THE EMBODIMENTS

Figure 1:
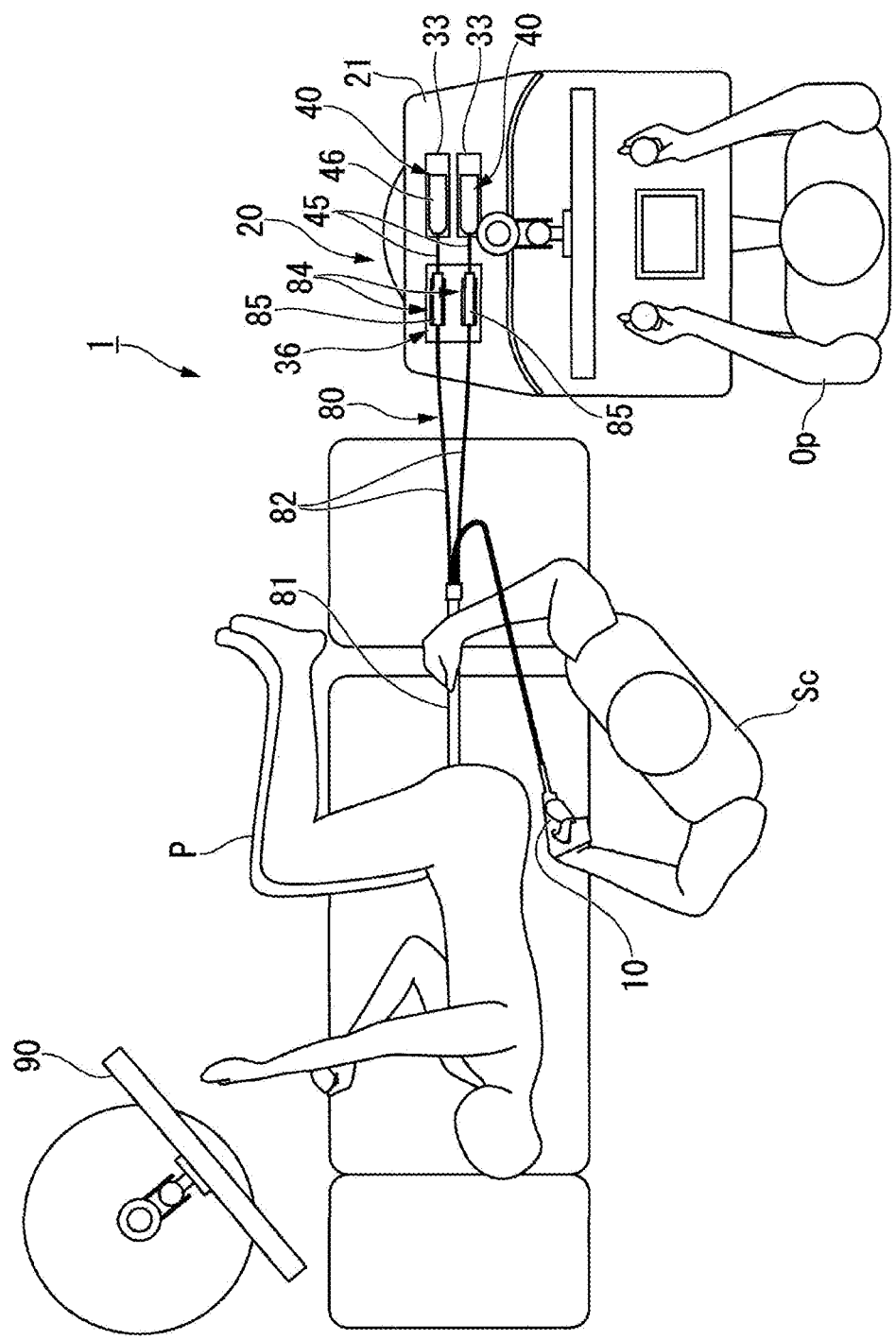
FIG. 1 illustrates a top view of a medical system used to operate on a body of a patient according to a first embodiment of the technology disclosed herein.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

One of the significant disadvantages of medical devices operating under remote control is that they are supported on instruments that are different from the medical devices. Therefore, when a medical device operates, frictional resistance occurs between the medical device and the instrument that supports the medical device. The frictional resistance increases if there is a large positional misalignment between the medical device and the instrument that supports the medical device.

Therefore, there is a need for medical systems having various medical devices that eliminate or at least significantly reduce the frictional resistance between the medical devices and the instruments that support the medical devices.

The technology disclosed herein is directed to a medical system, a medical over-tube, and a medical device adapter that permits a medical device to operate smoothly and eliminates or significantly reduces frictional resistance between the medical device and another instrument to which the medical device is connected.

According to a first aspect of the technology disclosed herein, a medical system includes a medical device, -medical over-tube, and a console. The medical device includes an insertion portion protected by the medical over-tube for inserting the insertion portion into the body of a patient. The medical device is insertable through the over-tube. The console includes a first connector connectable to the medical device and a second connector connectable to the over-tube. The over-tube includes a tubular main body and a proximal-end portion. The insertion portion of the medical device is insertable through the tubular main body. The proximal-end portion is connected to the tubular main body and connectable to the second connector. The proximal-end portion includes a tubular member, a base portion, and a moving mechanism. The tubular member includes an insertion port for inserting the insertion portion of the medical device therethrough. The base portion is connected to the second connector. The moving mechanism interconnects the tubular member and the base portion so as to cause the tubular member to move with respect to the second connector such that the tubular member has two or more degrees of freedom with respect to the second connector.

The tubular member may support the insertion portion such that the insertion portion can be turned about the central axis thereof. The moving mechanism may be capable of turning the tubular member about two axes (i) that are perpendicular to the central axis of the insertion portion which is inserted in the tubular member and (ii) that are perpendicular to each other.

The base portion may be part of the moving mechanism by being connected to the second connector such that the base portion can be turned about a predetermined axis with respect to the second connector.

The moving mechanism may have a coupling which couples the tubular member and the base portion to each other. The coupling may include a first pivot portion and a second pivot portion. The first pivot portion is coupled to the tubular member such that the first pivot portion is turned with respect to the tubular member about an axis perpendicular to the predetermined axis. The second pivot portion is coupled to the base portion such that the second pivot portion is turned with respect to the base portion about an axis parallel to the axis of the first pivot portion.

The moving mechanism may have a flexible deformable member and a tubular coupling main body. The flexible deformable member is attached to the tubular member. The tubular coupling main body is attached to the flexible deformable member and is coupled to the base portion in coaxial relation to the tubular member.

The base portion may be part of the moving mechanism by being connected to the second connector such that the base portion is turned about a predetermined axis with respect to the second connector. The base portion may have a pivot portion and a support portion. The pivot portion is coupled to the tubular coupling main body such that the tubular coupling main body is turned with respect to the base portion about an axis perpendicular to the predetermined axis. The support portion is engageable with at least one of a plurality of positions arrayed in a direction along which the predetermined axis extends. The support portion is held in contact with the tubular coupling main body for limiting a range in which the tubular coupling main body can be turned.

According to a second aspect of the technology disclosed herein, a medical over-tube includes a tubular main body and a proximal-end portion. The tubular main body is for inserting an insertion portion of a medical device therethrough. The proximal-end portion is connected to the tubular main body. The proximal-end portion includes a tubular member, a base portion, and a moving mechanism. The tubular member includes an insertion port for inserting the insertion portion of the medical device therethrough. The base portion is connected to an instrument different from the medical device. The moving mechanism interconnects the tubular member and the base portion so as to cause the tubular member to move with respect to the base portion such that the tubular member has two or more degrees of freedom with respect to the base portion.

According to a third aspect of the technology disclosed herein, a medical device adapter is configured to connect a medical device having an insertion portion to another instrument. The medical device adapter includes a tubular member, a base portion, and a moving mechanism. The tubular member includes an insertion port for inserting the insertion portion therethrough. The base portion is detachably connectable to the other instrument and is connected to the other instrument with one or more degrees of freedom. The moving mechanism interconnects the tubular member and the base portion so as to cause the tubular member to move with respect to the base portion such that the tubular member has one or more degrees of freedom with respect to the base portion.

FIG. 1 illustrates a top view of a medical system 1 (hereinafter, simply referred to as "system") used to operate on a body of a patient according to a first embodiment of the technology disclosed herein. The system 1 includes an endoscope 10, a console 21, treatment tool units 40, and an over-tube 80 all of which are directly or indirectly connected to one another to diagnose a medical condition on inside body of a patient (P). Although the technology disclosed herein is directed to a medical field, but one of ordinary skill in the art would appreciate that the technology disclosed herein can be applied to other fields of art such as industrial inspection field. The console 21 is operable by an operator (Op). The treatment tool units 40 are attached to the console 21. The endoscope 10 and the treatment tool units 40 are inserted through the over-tube 80. The endoscope 10 may be of any of various structures selected in view of their performance, purposes for which they are operated.

Figure 2:
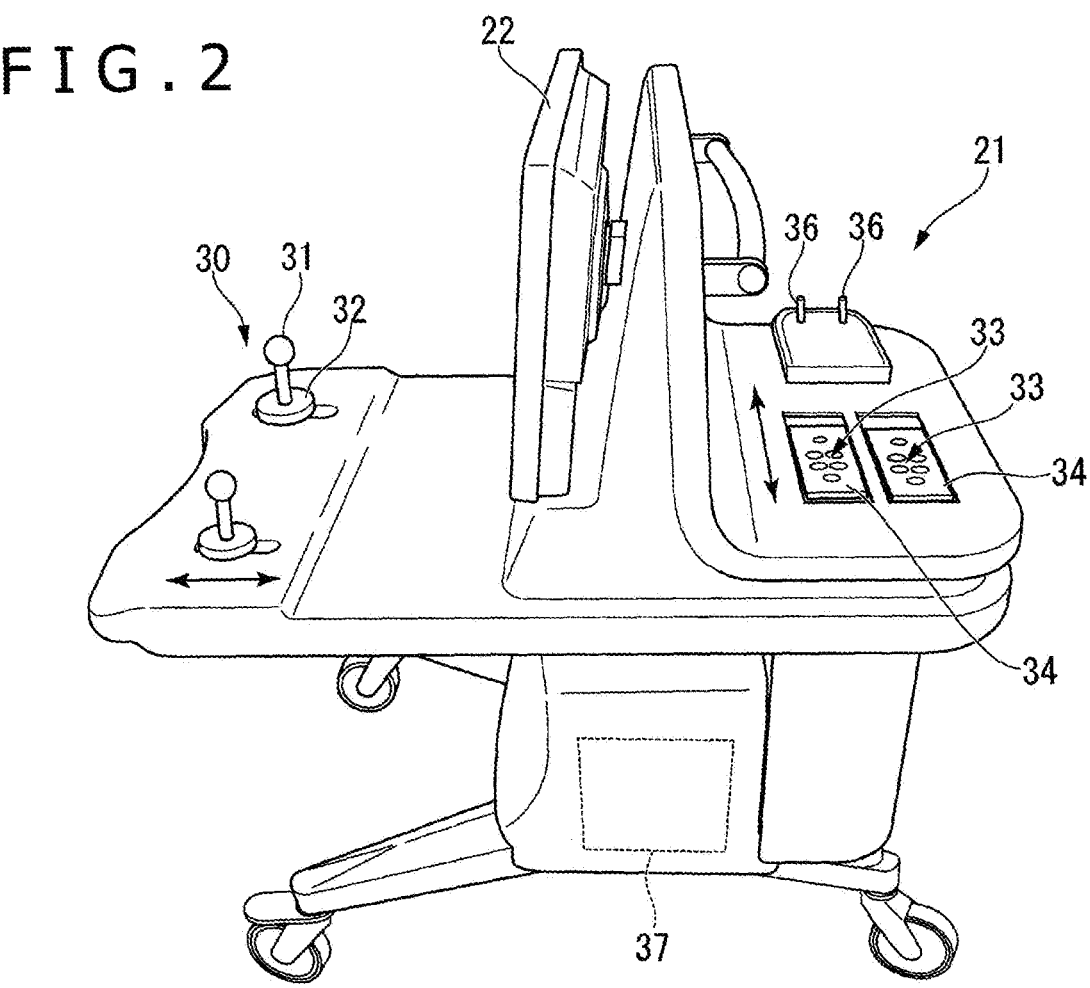
FIG. 2 is a perspective view of a console of the medical system shown in FIG. 1 according to the first embodiment.

FIG. 2 is a perspective view of the console 21 used in the system 1 as depicted in FIG. 1. The console 21 is used with the treatment tool units 40 and the over-tube 80 attached thereto when necessary. The console 21 includes a monitor 22, an operation unit 30, first connectors 33, second connectors 36, and a controller 37. The monitor 22 is connected to the endoscope 10. The operation unit 30 is operable by the operator (Op) to execute command inputs. The treatment tool units 40 are attached to the first connectors 33. The over-tube 80 is attached to the second connectors 36. The controller 37 operates the treatment tool units 40 based on outputs from the operation unit 30. As depicted in FIG. 2, the operation unit 30 has operation arms 31 and forward/backward operation units 32. The operation arms 31 are used to apply operations for the treatment tool units 40 as depicted in FIG. 1. The operation arms 31 are attached to the forward/backward operation units 32. The forward/backward operation units 32 are attached to the console 21 for relative movement with respect to the console 21. The forward/backward operation units 32 are physically connected to the first connectors 33, for example, by belts, chains, or the like. The forward/backward operation units 32 moves at a distance with respect to the console 21, and the first connectors 33 are movable in accordance with the distance with respect to the console 21. Alternatively, the first connectors 33 may be movable by electric motors or the like by respective distances commensurate with the distances that the forward/backward operation units 32 are moved forwards or backwards with respect to the console 21. In this embodiment, the treatment tool units 40 are attached to the console 21, but the treatment tool units 40 can be attached to a chassis that includes the first connectors 33, the second connectors 36, and the controller 37.

Figure 3:
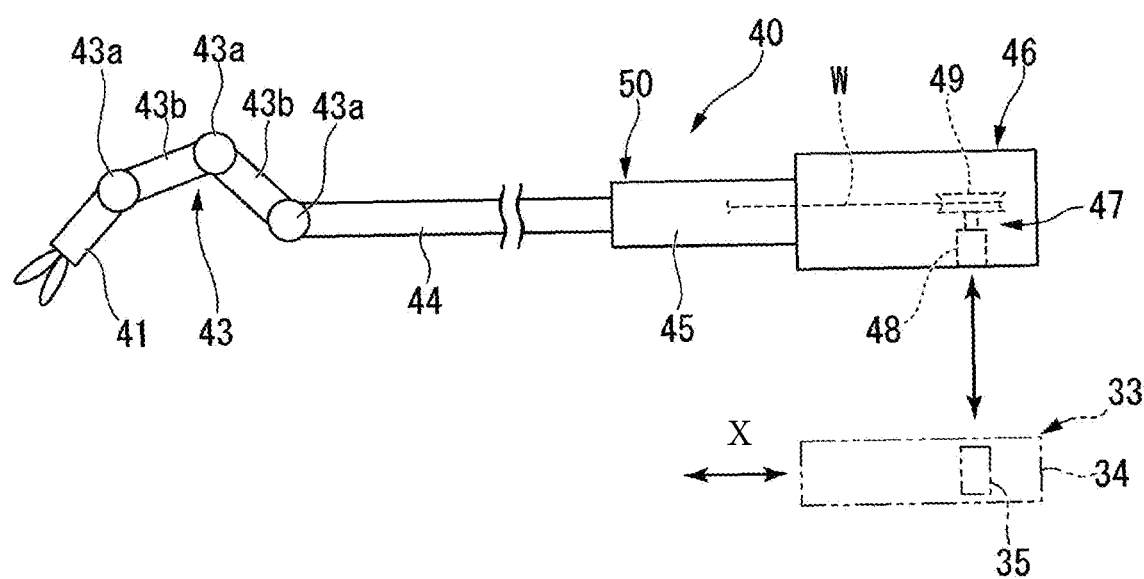
FIG. 3 is a side elevational view of a treatment tool unit to be attached to the console according to the first embodiment.

FIG. 3 is a view schematically depicting each of the treatment tool units 40. As depicted in FIGS. 2 and 3, each of the first connectors 33 includes a casing 34 and an electric motor unit 35. A motive power transmitting interface 46 of the treatment tool unit 40 is connected to the casing 34. The electric motor unit 35 is disposed in the casing 34. The casing 34 has hooks or the like, not depicted, for engagement with the motive power transmitting interface 46. The casing 34 is coupled to the forward/backward operation unit 32. Therefore, when the forward/backward operation unit 32 is moved relatively to the console 21, the casing 34 is moved relatively to the console 21 in interlocked relationship with respect to the forward/backward operation unit 32. The relative movement of the casing 34 with respect to the console 21 represents reciprocating movement in predetermined straight directions along a forward/backward axis as shown by the arrow in FIG. 3. The forward/backward axis of the casing 34 extends toward a corresponding one of the second connectors 36. While the motive power transmitting interface 46 is connected to the casing 34, the motive power transmitting interface 46 is also moved in unison with the movement of casing 34. The electric motor unit 35 has a plurality of electric motors and encoders, not depicted, that are connected to the controller 37. The electric motor unit 35 operates according to drive signals output from the controller 37. Motive power that is produced by the electric motor unit 35 under the control of the controller 37 is transmitted through an output shaft, not depicted, to the motive power transmitting interface 46. Each of the second connectors 36 is positioned on the forward/backward axis of the casing 34 of a corresponding one of the first connectors 33. The second connector 36 is in the form of a rod projecting outwardly from an outer surface of the console 21. The second connector 36 has a central axis extending perpendicularly to the forward/backward axis of the casing 34. The central axis of the second connector 36 extends vertically while the console 21 is appropriately installed on a floor, and serves as a central axis, or a yaw axis, about which an adapter 84 is angularly movable.

As depicted in FIGS. 2 and 3, the controller 37 is coupled to the operation arms 31, the electric motor units 35, and respective manipulators 43 of the treatment tool units 40. The controller 37 sends drive signals so as to operate the electric motor units 35. Each of the treatment tool units 40 is a medical device for performing a surgical treatment on a tissue that is a treatment-target region. The treatment tool unit 40 includes a treatment tool insertion portion 50 to be inserted into the body of the patient and a motive power transmitting interface 46 to be coupled to the treatment tool insertion portion 50. The motive power transmitting interface 46 is connectable to the first connector 33 for transmitting motive power to the manipulator 43. The treatment tool insertion portion 50 includes a treatment member 41, a manipulator or arm 43, and an elongated member or a soft member 44. The treatment member 41 is attached to the manipulator 43. The elongate member is defined by a soft member 44 and/or a hard member 45, for connecting the manipulator 43 and the motive power transmitting interface 46 to one another. Hereinafter, the side of the treatment tool unit 40 where the treatment member 41 is disposed will be referred to as a distal-end side, whereas the side of the treatment tool unit 40 where the motive power transmitting interface 46 is disposed will be referred to as a proximal-end side.

The treatment member 41 has one or more of various structures for incising, gripping, cauterizing, and suturing a tissue as a treatment-target region or the like. The treatment member 41 may be operated by the motive power which is transmitted through the motive power transmitting interface 46 to the treatment member 41. The manipulator 43 has a plurality of joints 43a and links 43b interconnecting the joints 43a to one another. The joints 43a are actuatable according to an operation input for the operation arm 31. The joints 43a are associated with encoders or the like for detecting respective angular displacements of the joints 43a.

When the operator (Op) operates the operation arm 31 into an optional configuration, the controller 37 actuates the joints 43a to bring the manipulator 43 into a configuration corresponding to the configuration of the operation arm 31. The joints 43a are actuated by the motive power which is transmitted through the motive power transmitting interface 46 to the manipulator 43. The soft member 44 is in the form of a pliable tube such as a resin tube, a coil sheath, or the like. The soft member 44 has a distal end connected to the manipulator 43. In addition, the soft member 44 houses therein a motive power transmitting member such as a wire w or the like extending from the motive power transmitting interface 46 to the manipulator 43.

Figure 4:
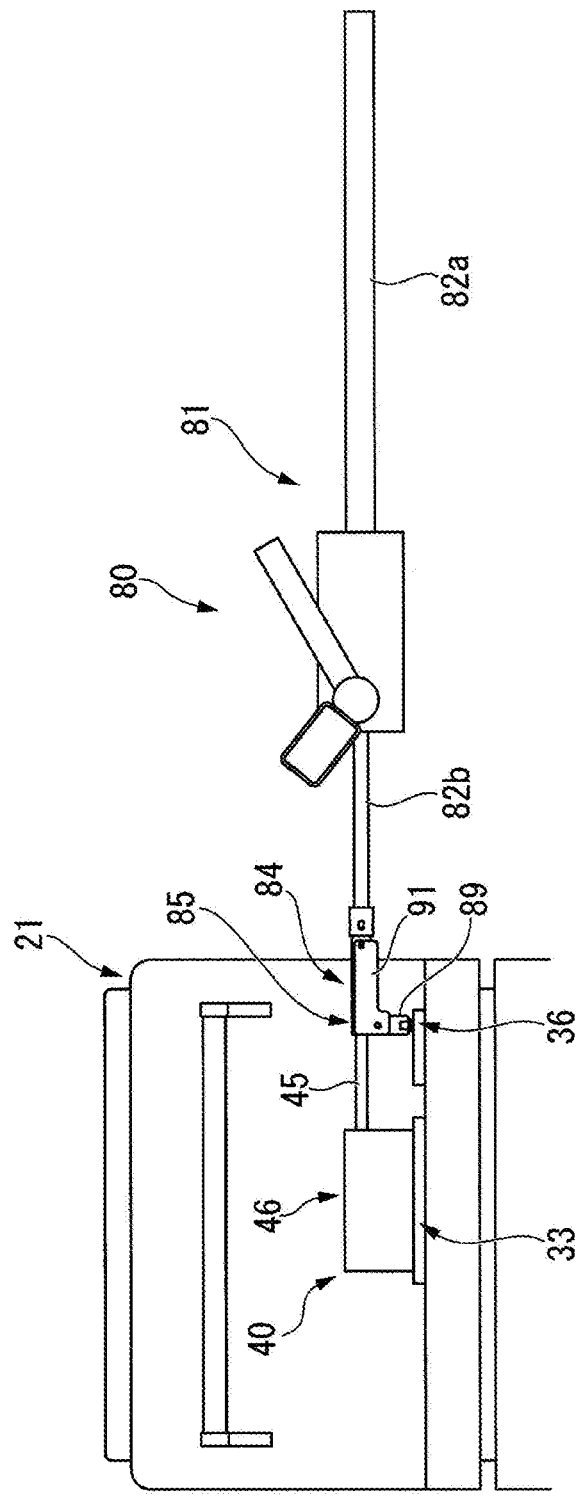
FIG. 4 is a side elevational view of an over-tube and the treatment tool unit being attached to the console according to the first embodiment.
Figure 5:
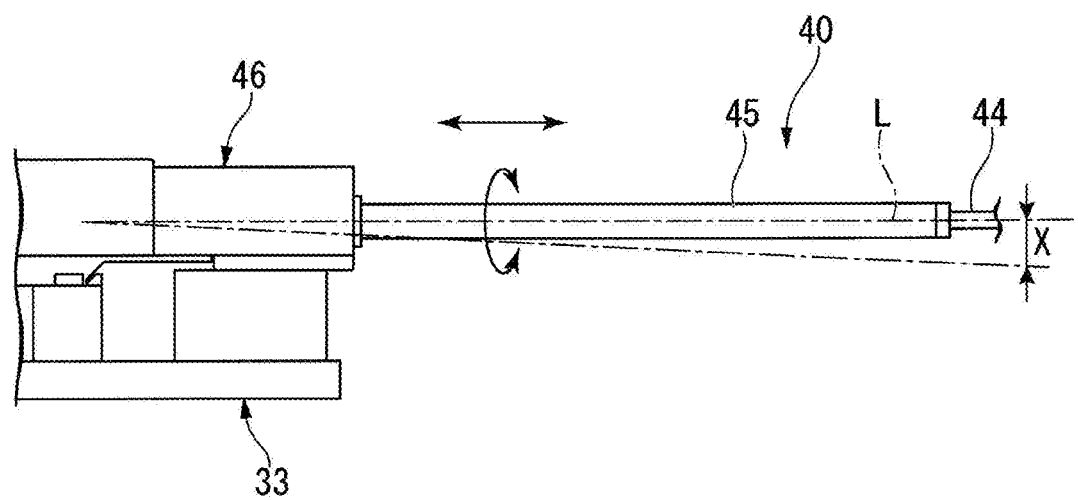
FIG. 5 is an enlarged side elevational view of a hard member and nearby parts of the treatment tool unit being attached to the console according to the first embodiment.

FIG. 4 is a side elevational view of the over-tube 80 attached to the console. FIG. 5 is an enlarged side elevational view of the hard member 45 and nearby parts of the treatment tool unit 40 attached to the console 21. As depicted in FIGS. 3 and 4, the hard member 45 is a hollow cylindrical hard member having a straight central axis as seen best in FIG. 3. The hard member 45 has a distal end to which the proximal end of the soft member 44 is attached. Forward and backward movement of the hard member 45 along the central axis thereof and the rotation of the hard member 45 about the central axis thereof are transmitted as forward and backward movement and rotation to the soft member 44. The inside of the hard member 45 is held in fluid communication with the inside of the soft member 44. The hard member 45 houses therein a motive power transmitting member such as a wire w or the like extending from the motive power transmitting interface 46 to the manipulator 43.

As depicted in FIG. 5, the hard member 45 of the treatment tool unit 40 is disposed such that the straight central axis L thereof lies horizontally. However, it is difficult to completely remove wobbling movement at the time the first connector 33 moved forwards and backwards along the forward/backward axis, flexure of the hard member 45 by its own weight. The central axis L of the hard member 45 may deviate a distance X, see FIG. 5, from the horizontal state thereof on account of wobbling movement, flexure. The motive power transmitting interface 46 is coupled to the proximal end of the hard member 45. The motive power transmitting interface 46 includes a plurality of motive power transmitting mechanisms 47 that are connectable to the electric motor unit 35 as seen best in FIG. 3. As depicted in FIG. 3, the motive power transmitting mechanisms 47 each has, among others, a coupling 48 and a pulley 49. The coupling 48 is rotatable by rotational drive power received from the output shaft of the electric motor unit 35. The pulley 49 is rotatable in unison with the coupling 48. The pulley 49 of the motive power transmitting mechanism 47 is operatively connected to the manipulator 43 by the wire (w) as the motive power transmitting member referred to hereinbefore. The motive power transmitting interface 46 transmits motive power for actuating the manipulator 43 through the wire (w) to the manipulator 43. One of the motive power transmitting mechanisms 47 is connected to the hard member 45 so as to be able to rotate the hard member 45 about the central axis thereof. Since the treatment member 41 is actuated by motive power generated by the electric motor unit 35, the motive power transmitting interface 46 includes a motive power transmitting mechanism, not depicted, for transmitting motive power from the electric motor unit 35 to the treatment member 41.

Figure 6:
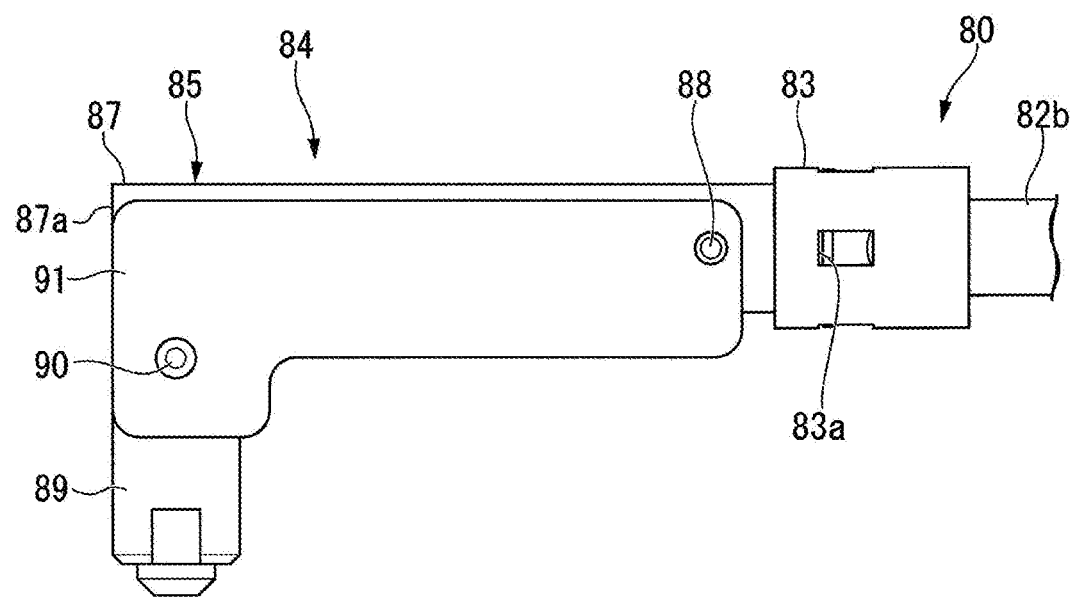
FIG. 6 is a side elevational view of a medical device adapter to be attached to the console according to the first embodiment.

As depicted in FIGS. 1 and 4, the over-tube 80 includes a tubular main body 81 and the adapter 84. The endoscope 10 and the treatment tool unit 40 are inserted through the tubular main body 81. The adapter 84 connects the over-tube 80 to the console 21. The main body 81 has an over-tube insertion portion 82a and a connecting tube 82b. The over-tube insertion portion 82a is inserted into the body of the patient. The connecting tube 82b interconnects over-tube insertion portion 82a and the adapter 84. The over-tube insertion portion 82a is in the form of a pliable tube. The over-tube insertion portion 82a includes a first lumen and a second lumen (Not shown in Figures). The endoscope 10 can be inserted through the first lumen from the opening at the proximal end of the first lumen in the over-tube insertion portion 82a. The treatment tool unit 40 can be inserted through the second lumen. The proximal end of the second lumen in the over-tube insertion portion 82a is held in fluid communication with the connecting tube 82b. The first lumen and the second lumen are open at the distal and proximal ends of the over-tube insertion portion 82a. The connecting tube 82b is in the form of a pliable tubular member having an inside diameter large enough to receive the treatment member 41 and the manipulator 43 therethrough. As depicted in FIG. 6, the connecting tube 82b includes an engaging member 83 for coupling the connecting tube 82b to a tubular member 85. The engaging member 83 has holes 83a formed therein for inserting therein hooks 85a disposed on the outer circumferential surface of a distal-end side of the tubular member 85. The adapter 84 is connected to the proximal end of the connecting tube 82b, and forms as a proximal-end portion of the over-tube 80. As depicted in FIG. 6, the adapter 84 includes the tubular member 85, a base 89 and a coupling 91. The base portion 89 interconnects the adapter 84 and the second connector 36, as seen best in FIG. 4. The coupling 91 interconnects the tubular member 85 and the base portion 89.

Figure 7:
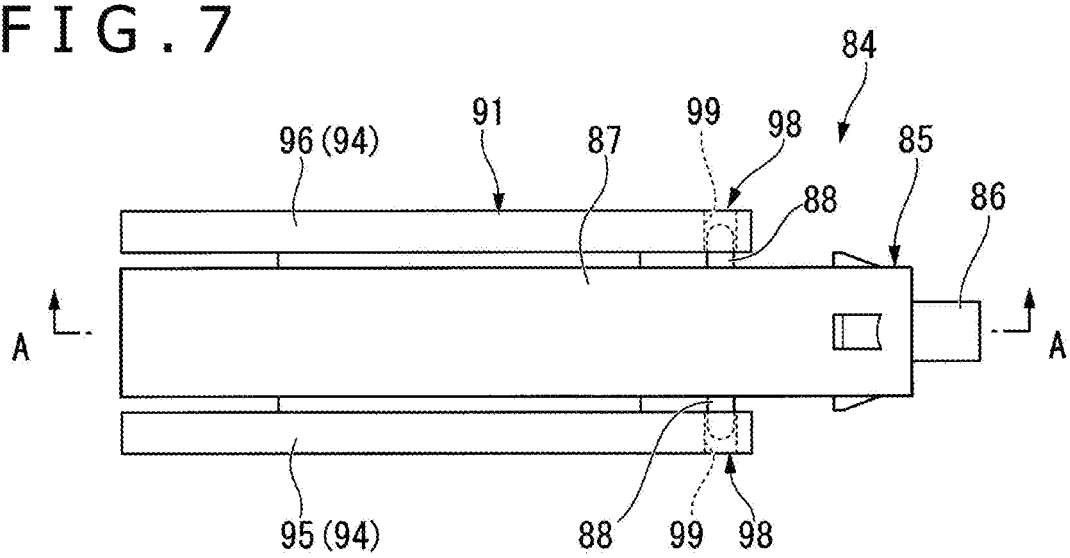
FIG. 7 is a plan view of the medical device adapter according to the first embodiment.
Figure 8:
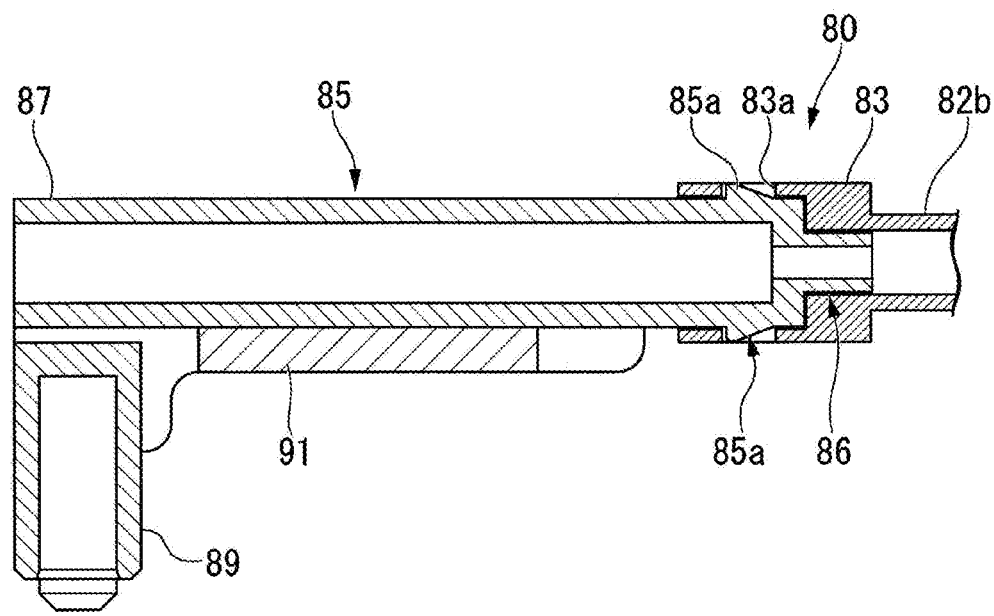
FIG. 8 is a cross-sectional view taken along line A-A of FIG. 7.

FIG. 7 is a plan view of the adapter 84 and FIG. 8 is a cross-sectional view taken along line A-A of FIG. 7. The tubular member 85 is a hard tubular member. The treatment member 41, the manipulator 43, and the soft member 44, can be received by the tubular member 85. The tubular member 85 has a tubular tube connector 86 and a large-diameter portion 87. The tubular tube connector 86 is connected to the connecting tube 82b. The large-diameter portion 87 has an inside diameter larger than the inside diameter of the tube connector 86. The tube connector 86 and the large-diameter portion 87 have respective central axes held in coaxial alignment with each other. The tubular member 85 has the hooks 85a that are inserted in the holes 83a in the engaging member 83 of the connecting tube 82b. According to the present embodiment, the hooks 85a are disposed closely to the distal end of the large-diameter portion 87. The tube connector 86 is a hollow cylinder through which the treatment member 41, the manipulator 43, and the soft member 44 are received.

Figure 9:
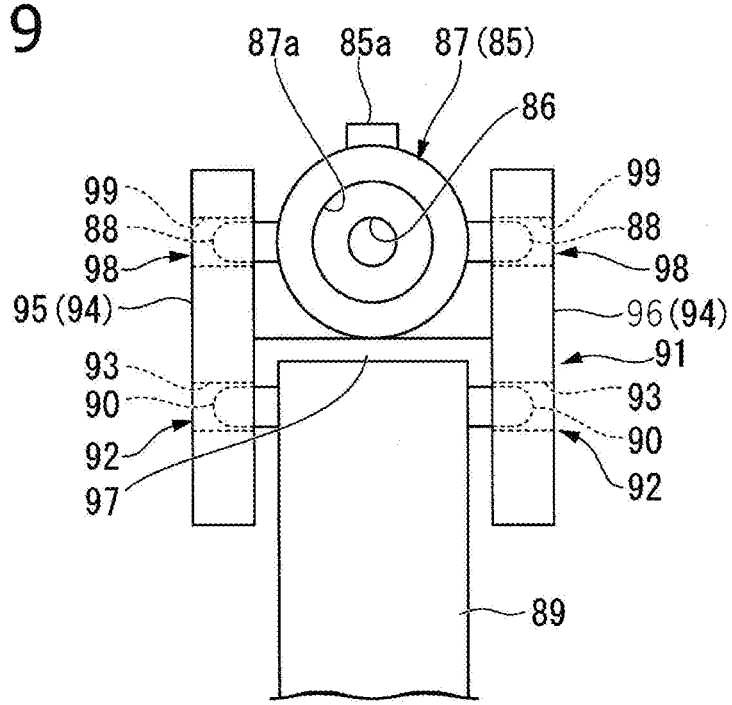
FIG. 9 is a rear elevational view of the medical device adapter according to the first embodiment.
Figure 10:
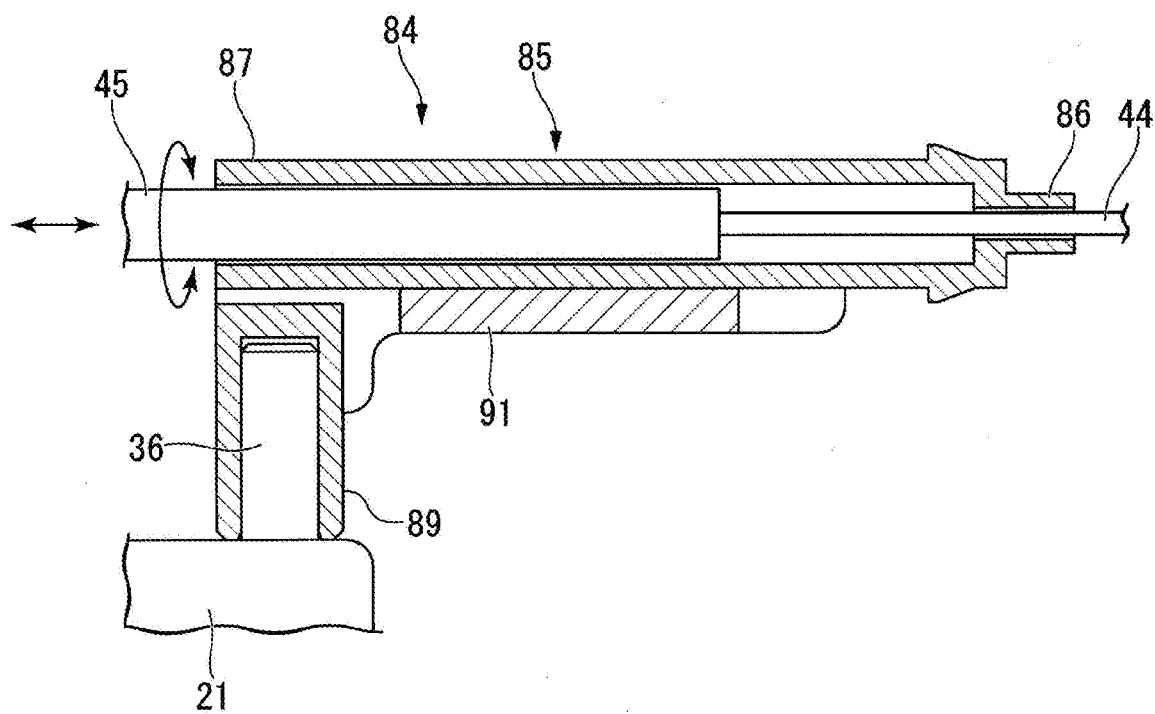
FIG. 10 is a partly cross-sectional view of the medical device adapter and the treatment tool unit installed thereon according to the first embodiment.

FIG. 9 is a rear elevational view of the adapter 84 and FIG. 10 is a partly cross-sectional view of the adapter 84 and the treatment tool unit attached thereto. The large-diameter portion 87 is a hollow cylinder through which the hard member 45 is received. The large-diameter portion 87 has a pair of pivot shafts 88 projecting from an outer circumferential surface of the tubular member 85 in straight directions perpendicular to the central axis of the large-diameter portion 87. The large-diameter portion 87 is joined to the coupling 91 by the pivot shafts 88. The large-diameter portion 87 has an insertion port 87a defined in a proximal end thereof for inserting the treatment tool units 40 therethrough into the tubular member 85. The large-diameter portion 87 has an inside diameter slightly larger than the outside diameter of the hard member 45. The large-diameter portion 87 contains the hard member 45 therein such that the respective central axes of the large-diameter portion 87 and the hard member 45 are held in substantially coaxial alignment with each other. The hard member 45 can be moved forwards and backwards with respect to the adapter 84 in directions along the central axis of the large-diameter portion 87. Furthermore, the hard member 45 can be rotated with respect to the adapter 84 about the central axis of the large-diameter portion 87. The central axis of the large-diameter portion 87 defines the position and orientation of a roll axis of the hard member 45, or the central axis of the hard member 45. As depicted in FIG. 4, the base portion 89 can be connected to the second connector 36 disposed on the console 21. The base portion 89 is of a tubular shape into which the second connector 36 is inserted. As depicted in FIGS. 6 and 9, the base portion 89 has a pair of pivot shafts 90 projecting outwardly from an outer circumferential surface of the base portion 89 along straight directions inclined to the central axis of the base portion 89. The straight directions are straight directions perpendicular to the central axis of the base portion 89. The base portion 89 is coupled to the coupling 91 by the pivot shafts 90.

As depicted in FIG. 10, the base portion 89 is held on the second connector 36 such that the central axis of a tubular portion of the base portion 89 and the central axis of the second connector 36 are held in coaxial alignment with each other. The base portion 89 is capable of rotating with respect to the second connector 36 about the central axis of the second connector 36. The base portion 89 makes the tubular member 85 movable with respect to the second connector 36 about the central axis of the second connector 36. In other words, the base portion 89 forms as part of a moving mechanism for making the tubular member 85 movable with respect to the second connector 36. As depicted in FIGS. 6 and 9, the coupling 91 has a first bearing portion 92, a pair of walls 94, a bottom 97, and a second bearing portion 98. The first bearing portion 92 has a bearing structure to which the respective pivot shafts 90 of the base portion 89 are coupled. Each of the pair of walls 94 is contiguous to the first bearing portion 92 and is spaced apart from each other. The bottom 97 interconnects the pair of walls 94. The second bearing portion 98 is disposed in the walls 94 and coupling the walls 94 to the pivot shafts 88 of the tubular member 85. The first bearing portion 92 has a pair of recesses 93 forming as bearings in which the pivot shafts 90 of the base portion 89 are inserted. With the pivot shafts 90 inserted in the recesses 93 of the first bearing portion 92, the coupling 91 is rotated with respect to the base portion 89 about a straight line interconnecting the pair of recesses 93. The walls 94 include a first wall 95 and a second wall 96 that are spaced apart from each other by a clearance that is larger than the outside diameter of the tubular member 85. The tubular member 85 can enter between the first wall 95 and the second wall 96. The second bearing portion 98 has a pair of recesses 99 forming as bearings in which the pivot shafts 88 of the tubular member 85 are inserted. With the pivot shafts 88 of the tubular member 85 inserted in the recesses 99 of the second bearing portion 98, the tubular member 85 is rotated with respect to the coupling 91 about a straight line interconnecting the pair of recesses 99 to one another. The base portion 89, the coupling 91, the first bearing portion 92, and the second bearing portion 98 are jointly making up the moving mechanism for permitting the tubular member 85 movable with respect to the second connector 36. The positional relationship between the first connector 33, the second connector 36, the treatment tool unit 40, and the adapter 84 of the system 1 according to the present embodiment is now described hereinafter.

As depicted in FIGS. 1, 2, and 4, the first connector 33 and the second connector 36 have their positions determined such that the central axis of the hard member 45 of the treatment tool unit 40 connected to the first connector 33 and the central axis of the tubular member 85 of the adapter 84 connected to the second connector 36 are held in substantially coaxial alignment with each other. Moreover, with the treatment tool unit 40 connected to the first connector 33 as depicted in FIG. 1 and the adapter 84 connected to the second connector 36 as depicted in FIG. 10, a portion of the treatment tool unit 40 which includes the distal end of the hard member 45 is positioned in the large-diameter portion 87 of the tubular member 85. The position of the first connector 33 with respect to the console 21 and the position and orientation of the forward/backward axis thereof may be finely adjustable.

Figure 11:
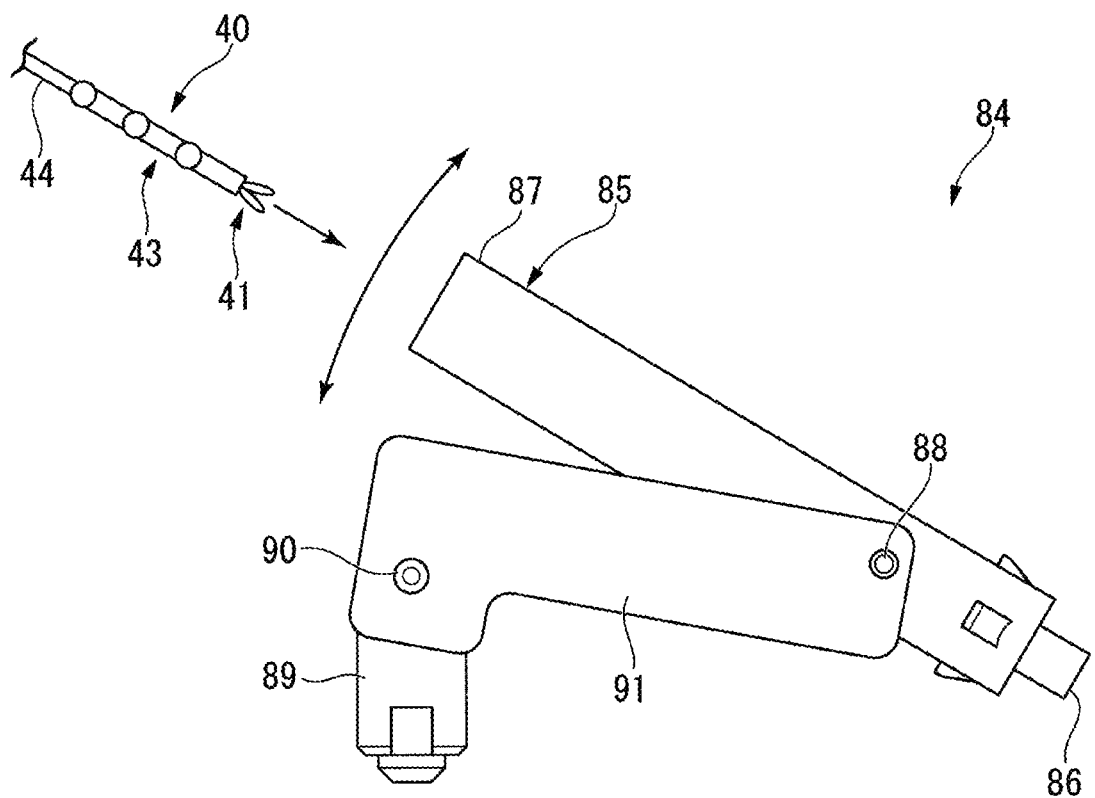
FIG. 11 is a side elevational view depicting the manner in which the medical device adapter rotates with respect to the treatment tool unit according to the first embodiment operates.
Figure 12:
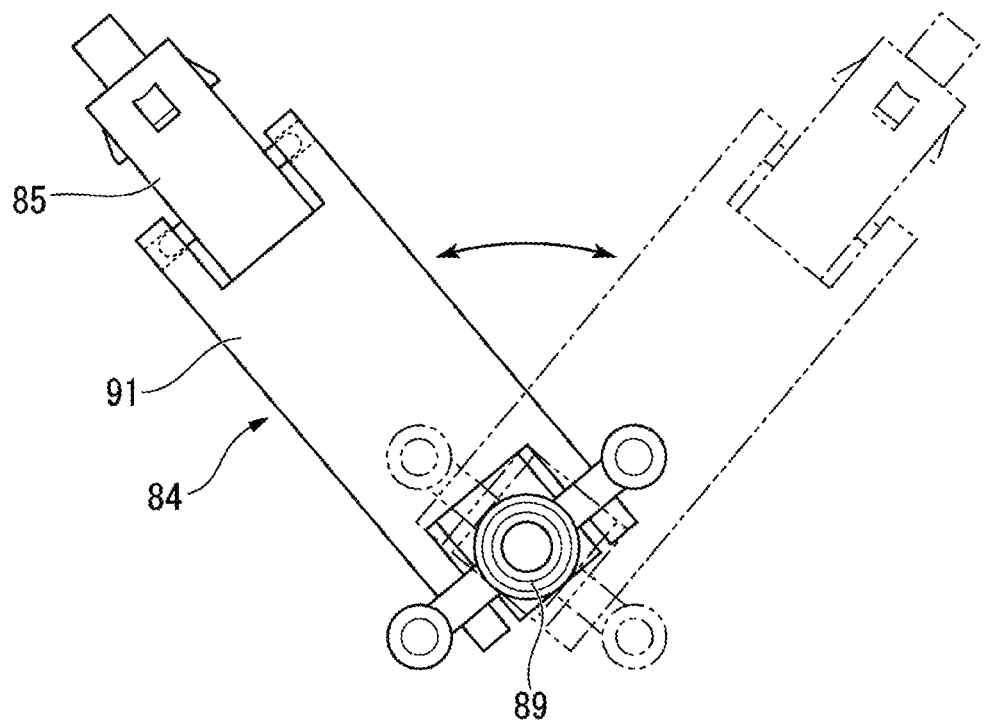
FIG. 12 is a bottom view of the medical device adapter according to the first embodiment operates.

Operation of the medical device adapter according to the present embodiment is now described. FIGS. 11 and 12 are side elevational views depicting the manner in which the medical device adapter according to the present embodiment operates. For using the system 1 according to the present embodiment, the adapter 84 of the over-tube 80 is connected to the second connector 36 of the console 21, as seen best in FIG. 1. Then, the endoscope 10 is inserted into the over-tube 80. The distal end of the over-tube 80 together with the endoscope 10 is inserted into the body of the patient. The operator (Op) and a doctor or an endoscopist (Sc) who operates the endoscope 10 can now observe the inside of the body of the patient using the endoscope 10. For treating a treatment-target region using the treatment tool unit 40 of the system 1, the treatment tool unit 40 is inserted into the over-tube 80. First, as depicted in FIG. 11, the distal end of the treatment tool unit 40 or the treatment member 41 is inserted into the tubular member 85 of the adapter 84 of the over-tube 80. The treatment member 41, the manipulator 43, and the soft member 44 of the treatment tool unit 40 are guided from the tubular member 85 toward the distal end of the main body 81.

For inserting the treatment tool unit 40 into the tubular member 85, the tubular member 85 can be moved to a position where the treatment tool unit 40 can easily be inserted into the tubular member 85 when necessary. In this process, the adapter 84 is kept connected to the second member 36. For example, the operator grips the treatment tool unit 40 to be inserted into the tubular member 85. Then the operator may grip and move the tubular member 85 such that the central axis of the hard member 45 and the central axis of the tubular member 85 are held in coaxial alignment with each other.

As depicted in FIGS. 11 and 12, the tubular member 85 is smoothly movable in a range with a degree of freedom defined by the base portion 89, the first bearing portion 92, and the second bearing portion 98 that make up the moving mechanism. After the distal end of the hard member 45 has been inserted into the tubular member 85, as shown in FIG. 10, the hard member 45 can further be inserted into the tubular member 85 while the tubular member 85 is not gripped but is rendered movable. At this time, when the hard member 45 is moved, the tubular member 85 is moved in a manner to follow the movement of the hard member 45 within the range with the degree of freedom defined by the first bearing portion 92, the second bearing portion 98, and the base portion 89, such that the central axis of the hard member 45 and the central axis of the tubular member 85 are held in substantially coaxial alignment with each other.

Having finished placing the treatment tool unit 40 in the over-tube 80, the operator connects the motive power transmitting interface 46 to the first connector 33, as depicted in FIG. 1. The treatment tool unit 40 is now ready to use. At this time, the central axis of the hard member 45 lies substantially parallel to the forward/backward axis of the first connector 33. When the treatment tool unit 40 is ready to use, (i) a portion of the treatment tool unit 40 which includes the proximal end of the soft member 44 is positioned in the tubular member 85, and (ii) a portion of the treatment tool unit 40 which includes the proximal end of the hard member 45 is positioned in the tubular member 85. With this arrangement, the distal end of the hard member 45 is in a position spaced toward the large-diameter portion 87 from the boundary between the large-diameter portion 87 and the tube connector 86 in a central-axis direction of the tubular member 85.

While the treatment member 41 is not in use though the treatment tool unit 40 is inserted in the over-tube 80, the distal end of the treatment tool unit 40 is not projected from the distal end of the main body 81. For example, when the treatment tool unit 40 is installed on the over-tube 80, the treatment member 41 is positioned within the main body 81 next to the distal end thereof. Upon forward and backward movement of the first connector 33, the motive power transmitting interface 46 moves forwards and backwards in unison with the first connector 33. The hard member 45 connected to the motive power transmitting interface 46 thus moves forwards and backwards in a direction along the forward/backward axis due to the forward and backward movement of the first connector 33.

In the medical system 1 according to the present embodiment, the first connector 33 and the second connector 36 have their positions determined in advance such that the central axis of the hard member 45 of the treatment tool unit 40 connected to the first connector 33 and the central axis of the tubular member 85 are held in substantially coaxial alignment with each other. Therefore, the hard member 45 moves smoothly forwards and backwards in the tubular member 85 upon forward and backward movement of the first connector 33. Furthermore, the central axis of the hard member 45 of the treatment tool unit 40 connected to the first connector 33 and the central axis of the tubular member 85 are held in substantially coaxial alignment with each other. Therefore, the hard member 45 rotates smoothly in the tubular member 85 when hard member 45 is rotated about the central axis thereof by rotational power transmitted from the motive power transmitting interface 46 to the hard member 45. Frictional resistance still exists between the outer circumferential surface of the hard member 45 and the inner circumferential surface of the tubular member 85 due to a positional misalignment between the hard member 45 and the tubular member 85. The positional misalignment is caused by (i) wobbling movement at the time the first connector 33 is moved forwards and backwards along the forward/backward axis and (ii) flexure of the hard member 45 by its own weight. The frictional resistance between the outer circumferential surface of the hard member 45 and the inner circumferential surface of the tubular member 85 increases as the positional misalignment between the central axis of the hard member 45 and the central axis of the tubular member 85 increases.

In the medical system 1 according to the present embodiment, when the central axis of the hard member 45 is displaced in position, the outer circumferential surface of the hard member 45 presses the inner circumferential surface of the tubular member 85. Then, the tubular member 85 moves smoothly in the direction in which the inner circumferential surface of the tubular member 85 is pressed because of one or more of the degrees of freedom of the first bearing portion 92, the second bearing portion 98, and the base portion 89 of the adapter 84. The degree of freedom provided by the base portion 89, or the degree of freedom that makes the base portion 89 angularly movable about the central axis of the second connector 36, corresponds to a yaw axis for the hard member 45 inserted in the tubular member 85. Furthermore, the degree of freedom provided by the first bearing portion 92 and the second bearing portion 98 corresponds to a pitch axis for the operation of the hard member 45. The first bearing portion 92 and the second bearing portion 98 allow the adapter 84 to move the hard member 45 in a direction along the yaw axis of the treatment tool unit 40. The tubular member 85 is moved in a manner to follow the movement of the central axis of the hard member 45 in order to reduce a positional misalignment between the position of the central axis of the hard member 45 and the position of the central axis of the tubular member 85. As a result, since a relative positional misalignment between the central axis of the hard member 45 and the central axis of the tubular member 85 is unlikely to increase in the medical system 1, the frictional resistance between the outer circumferential surface of the hard member 45 and the inner circumferential surface of the tubular member 85 is unlikely to increase. Therefore, even when the hard member 45 changes its position during operation of the treatment tool unit 40, the hard member 45 can smoothly move forwards and backwards and rotates in the tubular member 85.

The soft member 44, the manipulator 43, and the treatment member 41 are connected to the distal end of the hard member 45. The soft member 44, the manipulator 43, and the treatment member 41 smoothly operates in the medical system 1 because the hard member 45 can smoothly move forwards and backwards and rotates in the tubular member 85. Consequently, the response of the treatment tool unit 40 to an input applied to the operation unit 30 is then high, allowing the treatment tool unit 40 to perform a highly accurate treatment.

Figure 13:
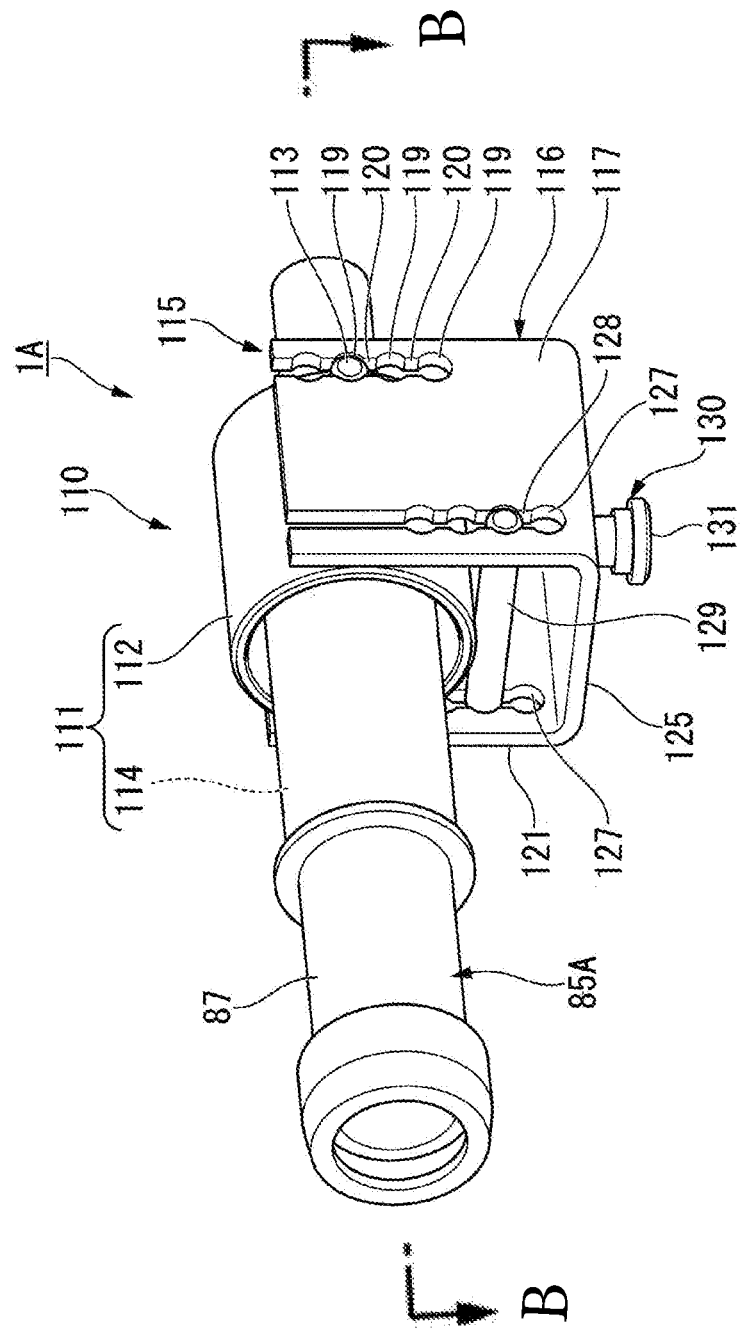
FIG. 13 is a perspective view of a medical device adapter according to a second embodiment of the present embodiment.

FIG. 13 is a perspective view of a medical device adapter of a medical system according to a second embodiment of the present embodiment. The medical system, denoted by 1A, according to the present embodiment, hereinafter referred to as "system 1A," includes an adapter 110 that is different in structure from the adapter 84 disclosed in the first embodiment. The medical system 1A according to the present embodiment has a console 21A (shown in FIG. 16) that is partly different in structure from the console 21 disclosed in the first embodiment. The console 21A is different from the console 21 in that it has a second connector 140 for attaching to the adapter 110 thereon. The second embodiment is identical to the first embodiment with respect to the other structures than the adapter 110 and the second connector 140. In the second embodiment, the components which correspond to those disclosed in the first embodiment are denoted by reference characters identical to those in the first embodiment, and redundant description thereof is omitted. As depicted in FIG. 13, the adapter 110 includes a tubular member 85A which is substantially similar to the tubular member 85 disclosed in the first embodiment, a coupling 111 joined to the tubular member 85A, and a base 115 joined to the coupling 111.

Figure 14:
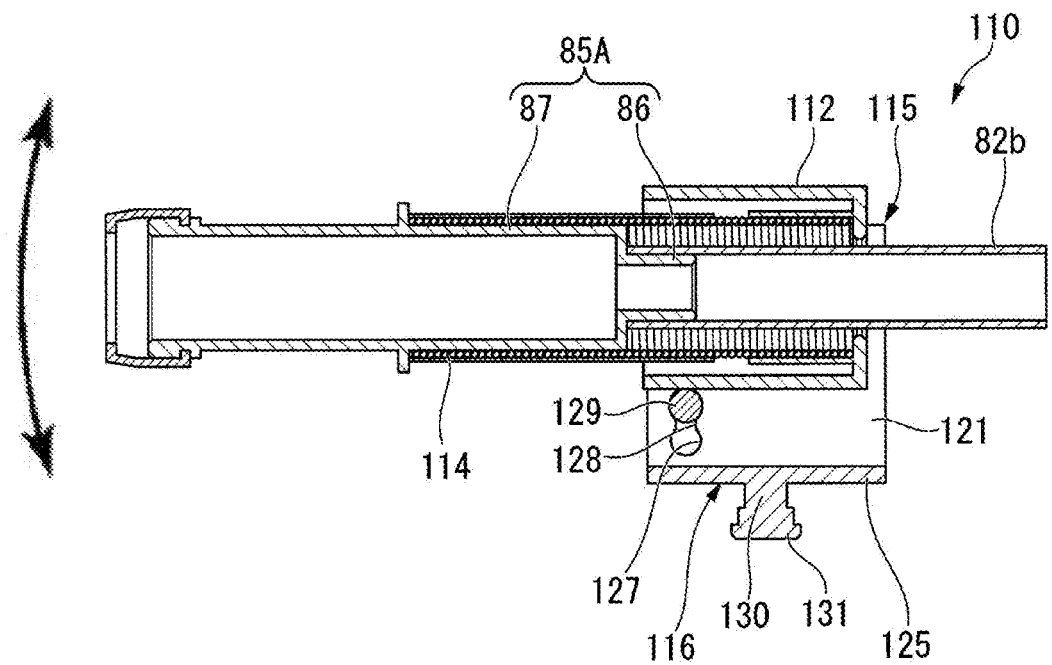
FIG. 14 is a cross-sectional view of the medical device adapter, taken along a line similar to line A-A of FIG. 7.
Figure 15:
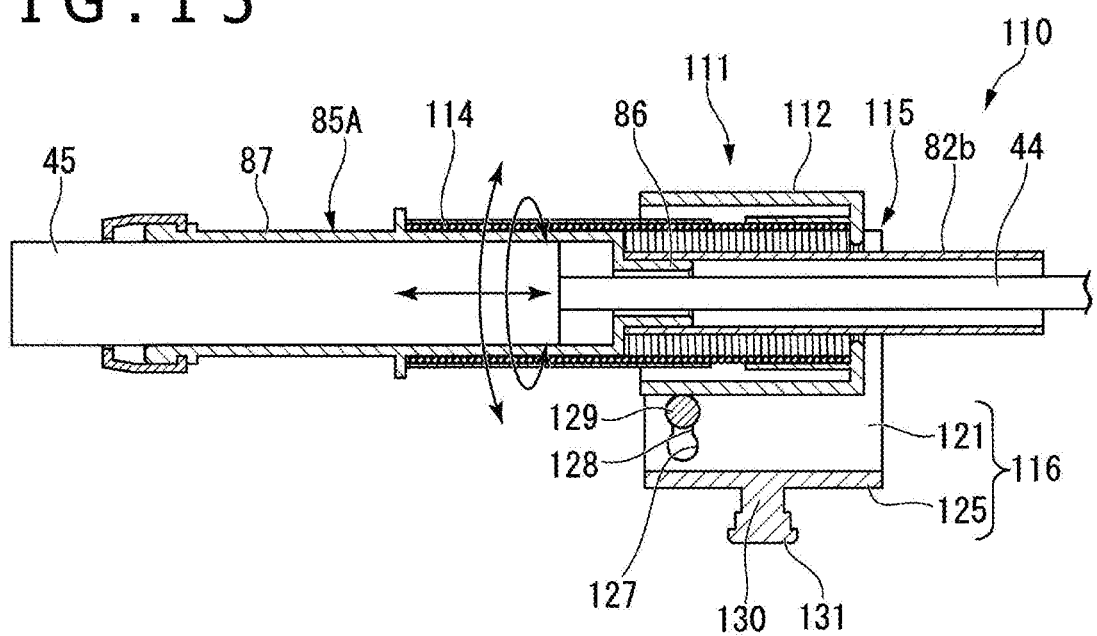
FIG. 15 is a partly cross-sectional view of the medical device adapter with the treatment tool unit installed thereon according to FIG. 14.

FIG. 14 is a cross-sectional view of the adapter 110, taken along a line similar to line A-A of FIG. 7 and FIG. 15 is a partly cross-sectional view of the adapter 110 with the treatment tool unit 40 installed thereon. The tubular member 85A is of a structure identical to the tubular member of the first embodiment in that it has the tube connector 86 and the large-diameter portion 87. The tubular member 85A is free of the pair of pivot shafts 88 disclosed in the first embodiment. The coupling 111 includes a hard tubular coupling main body 112 and a spring member 114 interconnecting the tubular member 85A and the coupling main body 112. The tubular member 85A and the coupling main body 112 are held by the spring member 114 such that the central axis of the coupling main body 112 and the central axis of the tubular member 85A are held in coaxial alignment with each other when no external forces are applied to the spring member 114. The coupling main body 112 has a pair of pivot shafts 113 projecting outwardly from an outer circumferential surface of the coupling main body 112 along straight directions perpendicular to the central axis of the coupling main body 112. The coupling main body 112 is coupled to the base portion 115 by the pair of pivot shafts 113.

The spring member 114 is an example of a flexible deformable member that is deformable under external forces. When subjected to external forces, the spring member 114 is deformed from its initial shape. When released from external forces, the spring member 114 restores its initial shape under restoring forces thereof. The spring member 114 is a coil spring having such an inside diameter that it can contact the outer circumferential surface of the large-diameter portion 87 of the tubular member 85A and such an outside diameter that it can contact the inner circumferential surface of the coupling main body 112. The spring member 114 is attached to the outer circumferential surface of the large-diameter portion 87 of the tubular member 85A. For example, the spring member 114 is attached to the outer circumferential surface of the large-diameter portion 87 by adhesive bonding, welding or the likes. Alternatively, the spring member 114 may be attached to the outer circumferential surface of the large-diameter portion 87 by having an inside diameter of the spring member 114 smaller than the outside diameter of the large-diameter portion 87. In this configuration, the spring member 114 is held in intimate contact with the outer circumferential surface of the large-diameter portion 87 under the resiliency of the spring member 114. The spring member 114 is attached to the inner circumferential surface of the coupling main body 112. For example, the spring member 114 is attached to a portion of the inner circumferential surface of the coupling main body 112 by adhesive bonding, welding or the likes. Alternatively, the spring member 114 may be attached to the inner circumferential surface of the coupling main body 112 by having an outside diameter of the spring member 114 larger than the inside diameter of the coupling main body 112. In this configuration, the spring member 114 is held in intimate contact with the inner circumferential surface of the coupling main body 112 under the resiliency of the spring member 114.

The base portion 115 includes a base main body 116, a shank 130, and an engaging member 131. The base portion main body 116 is joined to the coupling main body 112. The shank 130 defines an axis about which the base portion 115 can be turned with respect to the console 21A. The engaging member 131 is disposed on an end of the shank 130. The base portion main body 116 includes a first wall 117, a second wall 121, a bottom 125, and a position adjuster 126. The first wall 117 includes a first recess 118 defined therein that forms as a bearing in which one of the pivot shafts 113 of the coupling main body 112 is inserted. The second wall 121 is disposed in a position spaced from the first wall 117 and includes a second recess, not depicted, defined therein.

The second recess forms as a bearing in which one of the pivot shafts 113 is inserted. The bottom 125 interconnects the first wall 117 and the second wall 121. The position adjuster 126 is disposed in a position spaced from the recesses in the walls 117 and 121. The first wall 117 and the second wall 121 are spaced from each other widely enough to allow the coupling main body 112 to be inserted therebetween. The first recess 118 defined in the first wall 117 has a plurality of shaft fitting portions 119 disposed in positions that are different from each other along the central axis of the shank 130. Also, the first recess includes a passageway 120. In the first wall 117, the shaft fitting portions 119 are joined together by the passageway 120 slightly smaller than the diameter of the pivot shafts 113. The second wall 121 also includes shaft fitting portions 123 and a passageway 124 (not depicted in FIG. 13) that are similar to the shaft fitting portions 119 and the passageway 120 in the first wall 121. The shaft fitting portions 123 and a passageway 124 and the shaft fitting portions 119 and the passageway 120 are all mirror image of one another formed on first and second walls 117 and 121, respectively. The pivot shafts 113 of the coupling main body 112 are each inserted in the first recess 118 and the second recess, not depicted in FIG. 13. The position adjuster 126 is provided in the base portion 115 for adjusting the initial position of the coupling main body 112 such that the central axis of the coupling main body 112 is of a desired orientation. The position adjuster 126 includes a plurality of support fitting portions 127 and a support 129. The plurality of support fitting portion 127 is defined in the walls 117 and 121. The support 129 is in the form of a round rod fitted in some of the support fitting portions 127 and extending between the respective first and second walls 117 and 121.

The support fitting portions 127 are disposed in positions that are different from each other along the central axis of the shank 130. In the respective first and second walls 117 and 121, the support fitting portions 127 are joined together by passageways 128 slightly smaller than the diameter of the support 129. The support 129 is engageable with respective ones of the support fitting portions 127 in the respective first and second walls 117 and 121 such that the central axis of the support 129 extends along straight directions inclined to the central axis of the shank 130, i.e., straight directions perpendicular to the central axis of the shank 130 in the present embodiment. The diameter of the support 129 is slightly larger than the passageway 128. When the operator applies an external force sufficiently large to move the support 129 from one support fitting portion 127 to an adjacent support fitting portion 127, the support 129 can move in the passageway 128 against frictional resistance between the passageway 128 and the support 129. The support 129 has an outer circumferential surface that is brought into contact with the bottom 125 of the coupling main body 112. With the adapter 110 connected to the second connector 140, the support 129 is positioned below the coupling main body 112 which supports the coupling main body 112 from below. The support 129 is engageable with one of the support fitting portions 127 in each of the respective first and second walls 117 and 121. The support 129 is engageable with one of the support fitting portions 127 in the respective positions along a direction in which the central axis of the shank 130 extends. The coupling main body 112 is joined to the base portion main body 116 by the pair of pivot shafts 113, the first recess 118, and the second recess. The coupling main body 112 is turned with respect to the base portion main body 116 about a straight line interconnecting the pair of pivot shafts 113. Since the support 129 is disposed below the coupling main body 112, the support 129 prevents the coupling main body 112 from turning downwardly by the gravity force. In the absence of external forces on the coupling main body 112, the coupling main body 112 is held by the support 129, the first recess 118, and the second recess.

Depending on the position in which the support 129 is engageable with a support fitting portion 127, the angle of the central axis of the coupling main body 112 held in contact with the support 129 can be changed accordingly. The support 129 is engageable with one of the support fitting portions 127 in a certain position. The certain position is established such that the central axis of the tubular member 85A lies parallel to the forward/backward axis of the first connector 33 while the coupling main body 112 is held in contact with the support 129. The support 129 can be engageable with one of the support fitting portions 127 in a certain position. The certain position may be a position in which the central axis of the tubular member 85A lies horizontally while the coupling main body 112 is held in contact with the support 129. In this case, the range of angular movement of the coupling main body 112 is limited so as to prevent the large-diameter portion 87 side from being positioned below the tube connector 86. Moreover, in this configuration, the support 129 permits the coupling main body 112 to turn so as to cause the large-diameter portion 87 to be positioned above the tube connector 86. When both (i) the position in which the pivot shafts 113 are engageable with the shaft fitting portions 119 and 123 and (ii) the position in which the support 129 is engageable with the support fitting portions 127 are displaced the same distance along the central axis of the shank 130, the coupling main body 112 and the tubular member 85A are moved parallel along the central axis of the shank 130. The shank 130 is disposed on the bottom 125 of the base portion main body 116. The central axis of the shank 130 extends in a direction perpendicular to a straight line interconnecting the first recess 118 and the second recess (not depicted). The engaging member 131 is disposed adjacent to an end opposite to the bottom 125 side in the central axis of the shank 130. The engaging member 131 is in the form of a disk larger in diameter than the shank 130.

FIG. 16 is a schematic partly cross-sectional view depicting a configurational example of the console 21A to which the adapter 110 is to be attached. The second connector 140 of the console 21A includes a hole 141 and a retaining member 142. The shank 130 is to be inserted in the hole 141. The retaining member 142 is operable to move radially of the hole 141 to close a portion of the hole 141. Radial direction is depicted as an arrow in FIG. 16. The retaining member 142 is engageable with the engaging member 131 when the shank 130 is properly inserted in the hole 141. With the retaining member 142 engaged by the engaging member 131, the shank 130 is locked in the hole 141 against removal from the hole 141. The retaining member 142 is movable away from the engaging member 131 by an operating means, not depicted.

Figure 18:
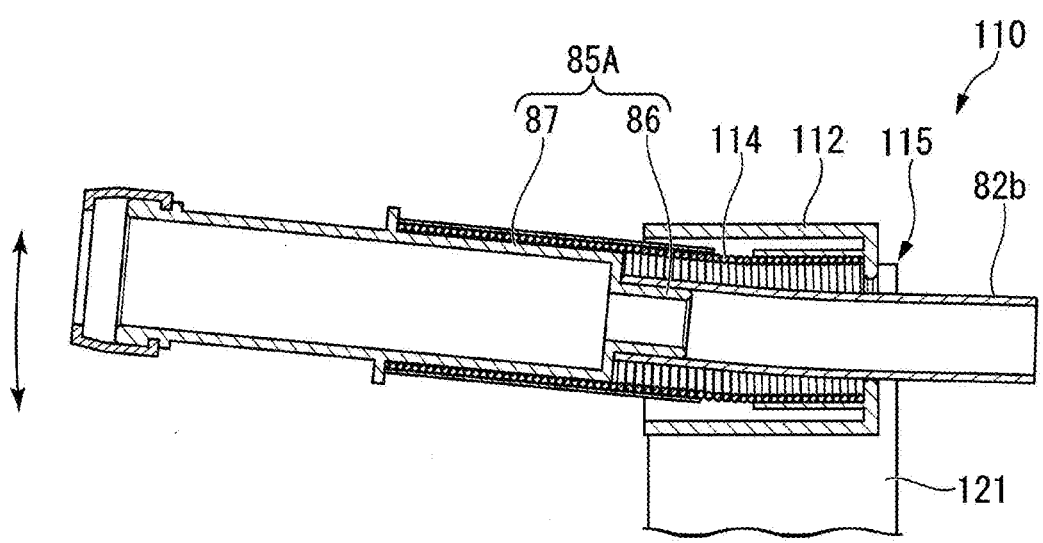
FIG. 18 is a cross-sectional view depicting the manner in which the medical device adapter operates.

Operation of the system 1A according to the present embodiment is now described hereinafter. FIGS. 17 and 18 are side elevational views illustrative of the manner in which the adapter 110 operates. According to the present embodiment, for installing the treatment tool unit 40 on the tubular member 85A, the tubular member 85A is moved with respect to the base portion 115 about the first recess 118 and the second recess as depicted in FIG. 17, so that the treatment tool unit 40 can smoothly be inserted into the tubular member 85A with the central axis of the hard member 45 and the central axis of the tubular member 85A being held in coaxial alignment with each other. The tubular member 85A can also be turned with respect to the console 21A about the central axis of the shank 130. After the distal end of the hard member 45 has been inserted into the tubular member 85A, as depicted in FIG. 15, the hard member 45 can further be inserted into the tubular member 85A while the tubular member 85A is not gripped but is rendered movable. At this position, when the hard member 45 is moved, the tubular member 85A is moved in a manner to follow the movement of the hard member 45 within the range with the degree of freedom defined by the coupling main body 112, the spring member 114, and the base portion 115, such that the central axis of the hard member 45 and the central axis of the tubular member 85A are held in substantially coaxial alignment with each other. The degree of freedom implemented by the base portion 115 corresponds to a yaw axis for the hard member 45 of the treatment tool unit 40 inserted in the tubular member 85A. Furthermore, the degree of freedom implemented by the first recess 118, the second recess, and the pair of pivot shafts 113 corresponds to a pitch axis for the operation of the hard member 45 of the treatment tool unit 40. Moreover, as depicted in FIG. 18, because of the spring member 114, the adapter 110 according to the present embodiment permits the hard member 45 to move three-dimensionally within the range in which the spring member 114 is elastically deformed.

In the system 1A according to the present embodiment, as described hereinbefore, the tubular member 85A is moved in a manner to follow the movement of the central axis of the hard member 45 in order to reduce a positional misalignment between the position of the central axis of the hard member 45 and the position of the central axis of the tubular member 85A. As a result, since a positional misalignment between the central axis of the hard member 45 and the central axis of the tubular member 85A is unlikely to increase in the system 1A, the frictional resistance between the outer circumferential surface of the hard member 45 and the inner circumferential surface of the tubular member 85A is unlikely to increase. In the system 1A, therefore, the hard member 45 can smoothly move forwards and backwards and rotate in the tubular member 85A. As the coupling main body 112 and the tubular member 85A are connected to each other by the spring member 114, the hard member 45 is allowed to move freely within the elastic range of the spring member 114. Although the embodiments of the technology disclosed herein have been described with reference to the drawings, specific configurational details are not limited to those embodiments, but may include design changes or the like without departing from the scope of the invention. For example, the adapter disclosed in each of the above embodiments may be an adapter for connecting a known over-tube to a console. For example, a tubular member may be connected to the proximal end of a known over-tube by a connecting tube. Furthermore, the main body of an over-tube and an adapter may be detachably attached to each other or undetachably attached to each other. The spring member disclosed in the second embodiment described above may be replaced with a member that is deformable under external forces, as a deformable member, such as a flexible resin tube. The components illustrated in the above embodiments may be arranged in appropriate combinations. The present disclosure can alternatively be used as the structure of an installation region of a medical device in a medical system.

In sum, the disclosed technology is directed to a medical system comprises a medical device having an insertion portion. An over-tube is configured to receive the insertion portion of the medical device so as to be inserted into a body of a patient. A console having a first connector attached to the medical device and a second connector attached to the over-tube. The over-tube comprises a tubular main body and a proximal-end portion being coupled to the tubular main body. The proximal-end portion having a tubular member having an insertion port for receiving the insertion portion of the medical device therethrough. A base portion is coupled to the second connector and a moving mechanism is coupled to both the tubular member and the base portion. The moving mechanism is configured to cause the tubular member to move with respect to the second connector such that the tubular member has two or more degrees of freedom with respect to the second connector.

The tubular member is configured to support the insertion portion such that the insertion portion is turned about the central axis thereof. The moving mechanism is configured to turn the tubular member about two axes. The two axes are perpendicular to the central axis of the insertion portion that is inserted in the tubular member. The base portion is configured to form part of the moving mechanism by being connected to the second connector such that the base portion is turned about a predetermined axis with respect to the second connector. The moving mechanism comprises a first pivot portion coupled to the tubular member such that the first pivot portion is turned with respect to the tubular member about an axis perpendicular to the predetermined axis. A second pivot portion is coupled to the base portion such that the second pivot portion is turned with respect to the base portion about an axis parallel to the axis of the first pivot portion. The moving mechanism comprises a flexible deformable member attached to the tubular member. A tubular coupling main body is attached to the flexible deformable member and the tubular coupling main body is coupled to the base portion in coaxial relation to the tubular member. The base portion is configured to form part of the moving mechanism by being connected to the second connector such that the base portion is turned about a predetermined axis with respect to the second connector. The base portion comprises a pivot portion coupled to the tubular coupling main body such that the tubular coupling main body is turned with respect to the base portion about an axis perpendicular to the predetermined axis. A support portion is configured to confine a range in which the tubular coupling main body is turned by contacting the tubular coupling main body. The support portion is configured to engage with one of a plurality of positions arrayed in a direction along which the predetermined axis extends.

A medical over-tube used within an elongated medical device comprises a tubular main body configured to receive an insertion portion of the elongated medical device. A proximal-end portion is coupled to the tubular main body. The proximal-end portion comprises a tubular member having an insertion port configured to receive the insertion portion of the elongated medical device therethrough. A base portion is coupled to an instrument different from the elongated medical device. A moving mechanism is coupled to the tubular member and the base portion. The moving mechanism is configured to cause the tubular member to move with respect to the base portion such that the tubular member has two or more degrees of freedom with respect to the base portion.

The tubular member is configured to support the elongated medical device such that the elongated medical device is turned about the central axis thereof. The moving mechanism is configured to turn the tubular member about two axes. The two axes are perpendicular to the central axis of the elongated medical device which is inserted in the tubular member. The moving mechanism comprises a first pivot portion coupled to the tubular member such that the first pivot portion is turned with respect to the tubular member about an axis perpendicular to the predetermined axis. A second pivot portion is coupled to the base portion such that the second pivot portion is turned with respect to the base portion about an axis parallel to the axis of the first pivot portion. The moving mechanism comprises a flexible deformable member attached to the tubular member. A tubular coupling main body is attached to the flexible deformable member. The tubular coupling main body is coupled to the base portion in coaxial relation to the tubular member. The base portion comprises a pivot portion coupled to the tubular coupling main body such that the tubular coupling main body is turned with respect to the base portion about an axis perpendicular to the predetermined axis. A support portion is configured to confine a range in which the tubular coupling main body being turned by contacting the tubular coupling main body. The support portion is configured to engage with one of a plurality of positions arrayed in a direction along which the predetermined axis extends.

A medical device adapter for connecting a medical device to a chassis. The medical device adapter comprises a tubular member configured to receive an insertion portion of the medical device therethrough. A base portion is detachably coupled to the chassis with one or more degrees of freedom. A moving mechanism is coupled to the tubular member and the base portion. The moving mechanism is configured to cause the tubular member to move with respect to the base portion such that the tubular member has one or more degrees of freedom with respect to the base portion.

The tubular member is configured to support the medical device such that the medical device is turned about the central axis thereof. The moving mechanism is configured to turn the tubular member about two axes. The two axes are perpendicular to the central axis of the medical device which is inserted in the tubular member. The moving mechanism comprises a first pivot portion coupled to the tubular member such that the first pivot portion being turned with respect to the tubular member about an axis perpendicular to the predetermined axis. A second pivot portion is coupled to the base portion such that the second pivot portion being turned with respect to the base portion about an axis parallel to the axis of the first pivot portion. The moving mechanism comprises a flexible deformable member attached to the tubular member. A tubular coupling main body is attached to the flexible deformable member. The tubular coupling main body is coupled to the base portion in coaxial relation to the tubular member. The base portion comprises a pivot portion coupled to the tubular coupling main body such that the tubular coupling main body is turned with respect to the base portion about an axis perpendicular to the predetermined axis. A support portion is configured to confine a range in which the tubular coupling main body being turned by contacting the tubular coupling main body. The support portion is configured to engage with one of a plurality of positions arrayed in a direction along which the predetermined axis extends.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical system comprising:
a medical device having an insertion portion;
an over-tube configured to receive the insertion portion of the medical device so as to be inserted into a body of a patient; and
a console having a first connector attached to the medical device and a second connector attached to the over-tube,
wherein the over-tube comprising:
a tubular main body, and
a proximal-end portion being coupled to the tubular main body,
wherein the proximal-end portion comprising:
a tubular member having an insertion port for receiving the insertion portion of the medical device therethrough,
a base portion being coupled to the second connector, and
a moving mechanism coupled to both the tubular member and the base portion, the moving mechanism being configured to cause the tubular member to move with respect to the second connector such that the tubular member has two or more degrees of freedom with respect to the second connector; and
wherein the moving mechanism comprising:
a flexible deformable member attached to the tubular member, and
a tubular coupling main body attached to the flexible deformable member, the tubular coupling main body coupled to the base portion in coaxial relation to the tubular member.

2. The medical system according to claim 1, wherein:
the tubular member being configured to support the insertion portion such that the insertion portion is turned about a central axis thereof,
the moving mechanism being configured to turn the tubular member about two axes, and
the two axes are perpendicular to the central axis of the insertion portion that is being inserted in the tubular member.

3. The medical system according to claim 1, wherein the base portion being configured to form part of the moving mechanism by being connected to the second connector such that the base portion is turned about a predetermined axis with respect to the second connector.

4. The medical system according to claim 1, wherein:
the base portion configured to form part of the moving mechanism by being connected to the second connector such that the base portion is turned about a predetermined axis with respect to the second connector, and
the base portion comprising:
a pivot portion coupled to the tubular coupling main body such that the tubular coupling main body is turned with respect to the base portion about an axis perpendicular to the predetermined axis, and
a support portion configured to confine a range in which the tubular coupling main body being turned by contacting the tubular coupling main body, the support portion being configured to engage with one of a plurality of positions arrayed in a direction along which the predetermined axis extends.

5. A medical over-tube used within an elongated medical device, the medical overtube comprising:
a tubular main body configured to receive an insertion portion of the elongated medical device; and
a proximal-end portion coupled to the tubular main body,
wherein the proximal-end portion comprising:
a tubular member having an insertion port configured to receive the insertion portion of the elongated medical device therethrough,
a base portion coupled to an instrument different from the elongated medical device, and
a moving mechanism coupled to the tubular member and the base portion, the moving mechanism being configured to cause the tubular member to move with respect to the base portion such that the tubular member has two or more degrees of freedom with respect to the base portion; and wherein the moving mechanism comprising:
- a flexible deformable member attached to the tubular member, and
- a tubular coupling main body attached to the flexible deformable member, the tubular coupling main body coupled to the base portion in coaxial relation to the tubular member.

6. The medical over-tube according to claim 5, wherein:
the tubular member configured to support the elongated medical device such that the elongated medical device being turned about a central axis thereof, and
the moving mechanism configured to turn the tubular member about two axes, the two axes are perpendicular to the central axis of the elongated medical device which is inserted in the tubular member.

7. The medical over-tube according to claim 5, wherein the base portion comprising:
- a pivot portion coupled to the tubular coupling main body such that the tubular coupling main body being turned with respect to the base portion about an axis perpendicular to a predetermined axis, and
- a support portion configured to confine a range in which the tubular coupling main body being turned by contacting the tubular coupling main body,
the support portion being configured to engage with one of a plurality of positions arrayed in a direction along which the predetermined axis extends.

8. A medical device adapter for connecting a medical device to a chassis, the medical device adapter comprising:
- a tubular member configured to receive an insertion portion of the medical device therethrough;
- a base portion detachably coupled to the chassis with one or more degrees of freedom; and
- a moving mechanism coupled to the tubular member and the base portion, the moving mechanism being configured to cause the tubular member to move with respect to the base portion such that the tubular member has one or more degrees of freedom with respect to the base portion;

wherein the moving mechanism comprising:
- a flexible deformable member attached to the tubular member, and
- a tubular coupling main body attached to the flexible deformable member, the tubular coupling main body coupled to the base portion in coaxial relation to the tubular member.

9. The medical device adapter according to claim 8, wherein:
the tubular member being configured to support the medical device such that the medical device being turned about a central axis thereof,
the moving mechanism being configured to turn the tubular member about two axes, and
the two axes are perpendicular to the central axis of the medical device which is inserted in the tubular member.

10. The medical device adapter according to claim 8, wherein the base portion comprising:
- a pivot portion coupled to the tubular coupling main body such that the tubular coupling main body being turned with respect to the base portion about an axis perpendicular to a predetermined axis, and
- a support portion configured to confine a range in which the tubular coupling main body being turned by contacting the tubular coupling main body, the support portion being configured to engage with one of a plurality of positions arrayed in a direction along which the predetermined axis extends.

* * * * *